(12) United States Patent
Berul et al.

(10) Patent No.: US 10,925,474 B2
(45) Date of Patent: Feb. 23, 2021

(54) DELIVERY TOOL AND METHOD FOR DEVICES IN THE PERICARDIAL SPACE

(71) Applicant: CHILDREN'S NATIONAL MEDICAL CENTER, Washington, DC (US)

(72) Inventors: Charles Berul, Bethesda, MD (US); Justin Opfermann, Washington, DC (US); Axel Krieger, Alexandria, VA (US); Peter Kim, Washington, DC (US); Tanya Davis, Washington, DC (US); Bradley Clark, Bowie, MD (US)

(73) Assignee: CHILDREN'S NATIONAL MEDICAL CENTER, Washington, DC (US)

( * ) Notice: Subject to any disclaimer, the term of this patent is extended or adjusted under 35 U.S.C. 154(b) by 888 days.

(21) Appl. No.: 14/625,350

(22) Filed: Feb. 18, 2015

(65) Prior Publication Data

US 2015/0230699 A1    Aug. 20, 2015

Related U.S. Application Data

(60) Provisional application No. 61/940,551, filed on Feb. 17, 2014.

(51) Int. Cl.
*A61B 1/05* (2006.01)
*A61B 1/018* (2006.01)
(Continued)

(52) U.S. Cl.
CPC ............ *A61B 1/05* (2013.01); *A61B 1/00154* (2013.01); *A61B 1/018* (2013.01); *A61B 1/3132* (2013.01); *A61B 5/0084* (2013.01); *A61N 1/0592* (2013.01)

(58) Field of Classification Search
None
See application file for complete search history.

(56) References Cited

U.S. PATENT DOCUMENTS 4,270,549 A    6/1981    Heilman
4,991,578 A    2/1991    Cohen
(Continued)

OTHER PUBLICATIONS

Extended European Search Report dated Oct. 9, 2017 in Patent Application No. 15749268.7.
(Continued)

*Primary Examiner* — Pascal M Bui Pho
*Assistant Examiner* — Farouk A Bruce
(74) *Attorney, Agent, or Firm* — Oblon, McClelland, Maier & Neustadt, L.L.P.

(57) ABSTRACT

The present disclosure is a device and method associated with the delivery of medical devices in the pericardial space using a minimally invasive approach with direct visualization. More specifically, the device can be used to deliver permanent pacing, defibrillation and cardiac resynchronization leads, as well as leadless pacemakers for cardiac rhythm management to the epicardial surface of the heart. A subxiphoid procedure is proposed as a minimally invasive alternative to thoracotomy, while the delivery tool incorporates a camera for direct visualization of the procedure. The tool also incorporates a steerable catheter to provide selective control of the placement and orientation of the medical device in the pericardial space.

18 Claims, 14 Drawing Sheets

(51) Int. Cl.
*A61B 5/00* (2006.01)
*A61N 1/05* (2006.01)
*A61B 1/00* (2006.01)
*A61B 1/313* (2006.01)

(56) References Cited

U.S. PATENT DOCUMENTS

| | | | |
|---|---|---|---|
| 5,707,389 A * | 1/1998 | Louw | A61B 17/12022 600/106 |
| 7,398,781 B1 | 7/2008 | Chin | |
| 8,075,532 B2 | 12/2011 | Kassab et al. | |
| 2003/0187461 A1 | 10/2003 | Chin | |
| 2004/0059298 A1 | 3/2004 | Sanderson | |
| 2004/0087831 A1 | 5/2004 | Michels et al. | |
| 2004/0106896 A1 | 6/2004 | Lee et al. | |
| 2005/0271631 A1 | 12/2005 | Lee et al. | |
| 2006/0052660 A1 | 3/2006 | Chin | |
| 2006/0079934 A1 | 4/2006 | Ogawa et al. | |
| 2006/0149129 A1 | 7/2006 | Watts et al. | |
| 2006/0184048 A1 | 8/2006 | Saadat | |
| 2006/0189934 A1 * | 8/2006 | Kuracina | A61B 5/15003 604/110 |
| 2006/0229490 A1 | 10/2006 | Chin | |
| 2006/0235458 A1 | 10/2006 | Belson | |
| 2007/0088418 A1 | 4/2007 | Jacobson | |
| 2007/0232849 A1 | 10/2007 | Gertner | |
| 2007/0232882 A1 * | 10/2007 | Glossop | A61B 8/0841 600/407 |
| 2007/0265494 A1 * | 11/2007 | Leanna | A61B 1/00098 600/107 |
| 2008/0183080 A1 | 7/2008 | Abraham | |
| 2008/0281293 A1 * | 11/2008 | Peh | A61B 1/0052 604/523 |
| 2011/0060227 A1 | 3/2011 | Saadat | |
| 2011/0160530 A1 * | 6/2011 | Ratnakar | A61B 1/0005 600/104 |
| 2012/0035584 A1 | 2/2012 | Thompson-Nauman et al. | |
| 2012/0088968 A1 | 4/2012 | Gambhir et al. | |
| 2012/0197373 A1 | 8/2012 | Khairkhahan et al. | |
| 2012/0232339 A1 | 9/2012 | Csiky | |
| 2013/0041214 A1 * | 2/2013 | Maahs | A61B 1/05 600/104 |
| 2015/0190036 A1 | 7/2015 | Saadat | |

OTHER PUBLICATIONS

International Search Report and Written Opinion dated May 28, 2015 in PCT/US2015/016360.
Office Action dated Nov. 9, 2018, in Australian Patent Application No. 2015218223. (3 pages).

* cited by examiner

DELIVERY TOOL AND METHOD FOR DEVICES IN THE PERICARDIAL SPACE

CROSS-REFERENCE TO RELATED APPLICATIONS

This application claims priority to U.S. Provisional Application No. 61/940,551, filed Feb. 17, 2014, which is hereby incorporated by reference in its entirety.

BACKGROUND

1. Field of the Disclosure

The present disclosure is related to the field of cardiac rhythm therapy, and a device capable of delivering medical devices for cardiac pacing to the pericardial space under direct visualization and control via percutaneous approach.

2. Description of the Related Art

Cardiac pacing is utilized to stimulate the heart, and currently can be performed via two distinct approaches: transvenously to access the endocardium and direct surgical access to the epicardial surfaces. Cardiac pacemaker implantation in small children and patients with congenital heart defects presents unique challenges to the cardiologist and surgeon. These patients are often too small for insertion of pacemaker leads through a standard transvenous approach. Congenital anomalies of the heart or venous system may also prevent transvenous lead placement. In addition to small body habitus and limited venous capacitance, other contraindications to transvenous pacing include intracardiac shunts, venous obstruction, and complex venous anatomy with inability to access the right heart endocardium, mechanical tricuspid valve, as well as endocarditis. Patients with congenital heart disease and device-dependent primary electrical diagnoses are likely to require multiple invasive procedures over the course of a lifetime, with attendant cumulative risk of venous occlusion. Cardiac resynchronization therapy (CRT) for left ventricular failure and dyssynchrony can be performed via transvenous approach in adults and older children with structurally normal hearts, but may necessitate utilization of a sternotomy or thoracotomy for epicardial placement in smaller patients and/or those with particular forms of congenital heart disease.

Although many teenage patients are well served by transvenous pacemakers, epicardial pacing currently remains the conventional technique for infants and those with complex congenital heart disease. Epicardial pacing currently requires either a median sternotomy or thoracotomy to access the epicardial surfaces. The post-operative recovery typically entails multiple days in the intensive care unit with the commensurate costs and risks. Patients undergoing sternotomy are also at increased risk of intrathoracic adhesions with heightened subsequent operative risk of reentry injury should the need for reoperation/exploration arise. Re-operation can be difficult, as the fibrotic tissue must be fully dissected in order to reach viable cardiac tissue for acceptable pacing thresholds.

Most of the approved technology used to implant devices for managing cardiac rhythm disease, are delivered by a transvenous approach that relies on patient vasculature for navigation under intermediate exposure to fluoroscopy. For pediatric, single ventricle, and abnormal vasculature patients, a transvenous approach is not suitable due to restriction in anatomy used for navigation. As a result, patients are subjected to either thoracotomy or equivalent procedure to expose the heart, allowing direct access to the pericardium.

There are several existing patents that address exposure of the pericardium for the placement of epicardial devices and that propose the use of a minimally invasive approach to reduce patient trauma. U.S. Pat. No. 4,991,578 entitled "Method and System for Implanting Self-anchoring epicardial Defibrillation Electrode" introduces a catheter based delivery tool capable of penetrating the pericardium via percutaneous approach, along with a defibrillation lead that can be selectively anchored in the pericardial space.

U.S. Pat. No. 4,270,549 entitled "Method for Implanting Cardiac Electrodes" introduces a delivery tool and method to create a planar tunnel originating from the upper abdomen and terminating at the heart by use of a mandrel attached to a patch electrode, which is secured to the external surface of the heart. U.S. patent application Ser. No. 10/174,454 entitled "Releasable Guide and Method for Cardiac Lead Placement" proposes a similar endoscopic delivery tool capable of direct visualization of the pericardium, equipped with a working channel capable of delivering pericardial injections and leads. A subxiphoid delivery to minimize patient trauma is also detailed. In the future, leadless pacemakers will replace many of the permanent pacing, defibrillation, and cardiac resynchronization leads for both Endocardial and epicardial procedures. These medical devices will require specialized delivery tools to selectively place them throughout the heart for cardiac rhythm therapy. U.S. patent application Ser. No. 13/324,781 titled "Delivery Catheter Systems and Methods" details a catheter based delivery tool and feature based leadless pacemaker that can be selectively coupled for implantation. Likewise, U.S. patent application Ser. No. 11/549,574 "Delivery System for Implantable Biostimulator" details a second concept of selectively coupling a leadless pacemaker to a catheter based delivery tool, for implantation in the endocardium.

SUMMARY

The present disclosure differs from U.S. Pat. Nos. 4,991,578 and 4,270,549, at least, in that navigation and visualization is achieved with the use of a camera embedded in the delivery tool as opposed to intermittent fluoroscopic images gathered throughout the procedure. As a result, pericardial access is achieved under direct visualization of the tissue, reducing the risk of myocardial puncture, and excess radiologic exposure.

The present disclosure differs from the proposed technology in U.S. patent application Ser. No. 10/174,454, at least, in three ways. First, the delivery tool only offers visualization parallel to the working channel, reducing the capability of a surgeon to accurately gauge depth during pericardial puncture. Second, the delivery tool does not offer control of epicardial leads once inside in the pericardial space, limiting implantation to the ventricular surface. Third, two cannula are necessary to fixate a lead so only visualization outside of the pericardial space can be achieved.

The present disclosure differs from U.S. patent application Ser. Nos. 13/324,781 and 11/549,574, at least, in that these applications rely on vasculature and fluoroscopy for navigation and visualization of the tool, and do not feature the dexterity at the distal tip necessary for epicardial implantation.

There are currently no approved leads or delivery tools on the market for percutaneous pericardial pacing or defibrillator lead placement. Given the safety and efficacy of available transvenous and epicardial pacing leads, a novel pericardial lead and delivery system would need to demonstrate at least safety, feasibility, and non-inferiority. The proposed technology fulfills this unmet need by providing a tool and technique capable of direct, in-line, visualization while positioning medical leads and leadless pacemakers through a percutaneous approach to the pericardial space. The technology could also be adapted to improve the delivery of alternative medical devices for procedures such as pericardiocentesis and cardiac ablation from the epicardial surface.

Given the significant limitations of the current approaches for cardiac pacing, defibrillation, and resynchronization, a novel implantation tool and technique is described to allow minimally-invasive pericardial approach to the epicardial surfaces of the heart under direct in-line visualization. Using this tool and technique, a permanent pacing lead or leadless pacemaker can be positioned on the epicardium of the atrium and/or ventricle via a percutaneous access to the pericardium with direct visualization of critical cardiac structures.

Access is achieved by a subxiphoid approach where a trochar is introduced into the left thorax under direct visualization. The lung is then collapsed through the introduction of carbon dioxide ($CO_2$) insufflation. A camera with a working channel is introduced into the left thorax [pleural cavity?] providing visualization of the surface of the heart. With direct visualization of the camera, graspers, needles, and/or dilators can be used within the working channel to gain access to the pericardial space. After access is achieved, steerable catheters can be positioned within the working channel to selectively navigate and orient medical devices inside the pericardial space.

A single cannula allows the camera to be positioned within the pericardial space itself, providing direct visualization for navigation and anchoring of the medical device. With this approach, a lead can be selectively placed on the right or left atrial epicardium for atrial pacing, or the right and/or left ventricular epicardium for ventricular pacing, cardiac resynchronization therapy, and/or defibrillation. Clear visualization of the pericardium, the beating heart, and critical structures such as coronary arteries is critical to position cardiac devices securely and safely while avoiding cardiac and coronary injury in the pericardial space.

Subxiphoid pericardial pacing and defibrillator lead delivery would be beneficial to several important groups of patients, who may not be able to receive standard transvenous pacing systems. The following is a list of groups that may benefit from this approach; however, the list is not exhaustive.

A first group may be infants and small children, whose size precludes transvenous pacing and only currently have the option of an open-chest approach to the epicardium. If they require multisite pacing such as for cardiac resynchronization therapy, the open-chest access would need to be even larger or multiple in order to reach the atrium and both ventricles.

A second group may be patients with congenital heart disease. These patients may have contraindication to transvenous pacing due to intracardiac shunts or may have inaccessible endocardial surfaces due to abnormalities in venous or cardiac anatomy. Therefore, they also would not be amenable to transvenous pacing and would require open-chest access to place epicardial pacing leads. For defibrillation, there is not a suitable FDA-approved alternative, and they often undergo off-label indication use of current leads placed using an open-chest access to the pericardial space.

A third group may be any patient, regardless of size and anatomy that may benefit from a subxiphoid pericardial approach versus standard epicardial approach due to less invasive procedure reducing surgical morbidity, and potentially shortening recovery time and total expense of procedure.

A fourth group may be any patient, regardless of size and anatomy, which may benefit from a subxiphoid pericardial approach versus standard transvenous approach as it does not require venous access or fluoroscopy. This is particularly pertinent for those patients requiring left ventricular pacing leads through the coronary sinus system, where x-ray exposure can be substantial.

A fifth group may be any patient, regardless of size and anatomy, that may benefit from a subxiphoid pericardial approach if it is necessary to patch electrodes to the epicardial or pericardial surfaces of the heart, due to a less invasive technique, shorter recovery time, and total expense of procedure.

In some cases, the patient may not have a virgin pericardial sac to be accessed. Previous cardiac surgeries may result in the obliteration of the pericardial space all together. In this instance, a subxiphoid delivery tool may be beneficial to deliver multimodal imaging technology to the pericardial and epicardial surfaces of the heart. The multimodal imaging may include direct visualization, ultrasound transducers, multispectral light guide and camera, or any combination thereof. Use of multimodal imaging may help in the detection and identification of anatomical structures for safe and accurate placement of cardiac medical devices such as the coronary artery.

A subxiphoid approach may also be beneficial for the delivery of biological agents and therapeutic drugs to the pericardial space. In one application, the delivery of stem cells to the epicardium, pericardium, or pericardial space can be performed with a minimally invasive technique for selective placement under direct visualization. Pharmaceuticals can also be delivered directly to the epicardium, pericardium, or pericardial space with a minimally invasive technique for controlled, selective placement under direct visualization. In addition, procedures that require the access to the coronary arteries such as the placement of stents to remove obstructions will be possible with direct visualization in a subxiphoid approach. This approach will benefit patient groups such as infants and small children that are more susceptible to x-ray and have smaller vasculature, as well as the elderly who cannot tolerate an invasive open approach.

BRIEF DESCRIPTION OF DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

The present disclosure generally involves an apparatus and methods for delivering medical devices within the pericardial space. While several embodiments are disclosed, it is understood that the present disclosure is exemplary and can be embodied in many different forms. Therefore, the specific features and functionality of the tool disclosed are not to be interpreted as limiting, but to serve a basis for the claims, and to educate one skilled in the art as to the functionality of the tool with respect to the method of device delivery. For the purposes of teaching, the embodiments are direct towards the selective placement and implantation of cardiac leads and leadless pacemakers in the pericardial space, and should not be considered limiting.

Figure 1:
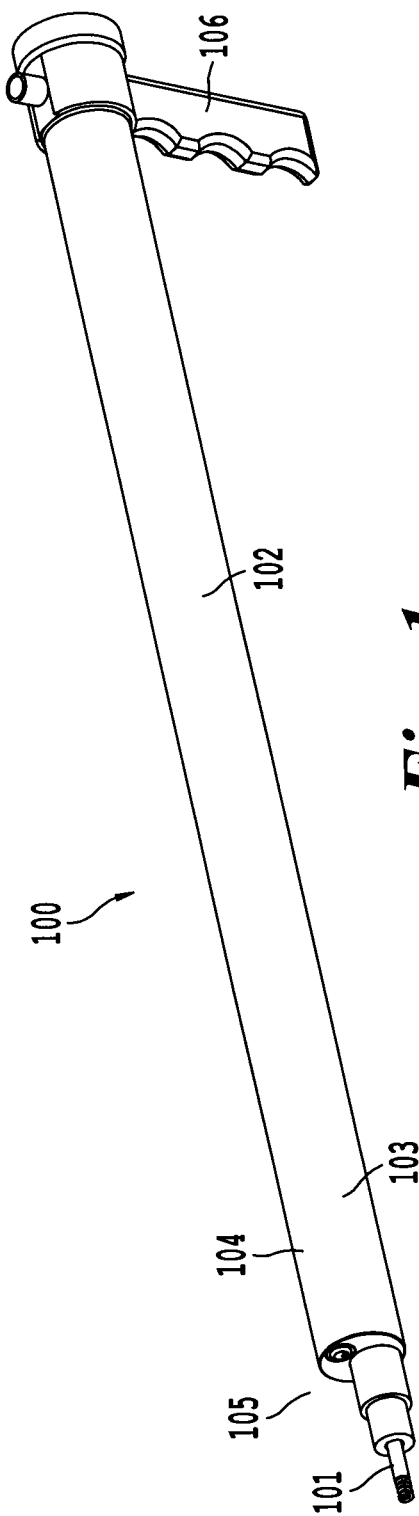
FIG. 1 illustrates an exemplary embodiment of a delivery tool configured or designed to deliver cardiac pacing leads.

FIG. 1 illustrates one embodiment of the proposed delivery tool 100 configured or designed to selectively deliver a cardiac device 101 into the pericardial space and epicardial surface. The core 102 of the delivery tool includes of a working channel 103 large enough to accommodate the medical device to be implanted including but not limited to cardiac pacing, defibrillation and resynchronization leads, pacemakers, leadless pacemakers, stem cells, needles, ablation catheters, biopsy punch, or other similar therapeutic devices. A second channel 104 includes a camera to provide direct visualization of the distal tip 105 when puncturing and anchoring the pacing lead within the pericardial space. The camera channel may contain a rigid camera that may have a fixed or adjustable viewing angle from 0-90°. Rotation and/or flexion of an angled or flexible camera may provide a wider field of view and enable a better direct visualization of the surgical site. The camera may also contain one or more working channels 111 through which surgical tools can be placed for the procedure. The core 102 is surrounded by a rigid shell that is used to hermetically seal the camera within the tool, and provide a rigid body that can be subcutaneously tunneled from a proximal incision to the heart. Alternatively, the tool 100 can be placed through a trochar that extends from the subxiphoid incision to the pleural space. The tool may be held by handle 106.

The medical device to be implanted is a pacemaker lead, implantable cardioverter-defibrillator (ICD) lead, pacemaker, leadless pacemaker, stem cells, needle, ablation catheter, biopsy punch or other similar therapeutic device.

Figure 2:
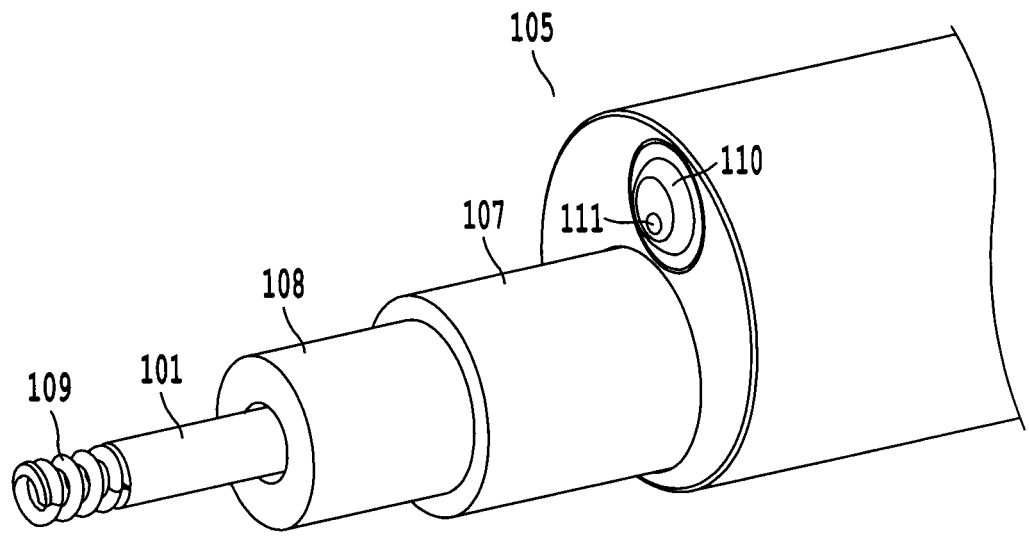
FIG. 2 illustrates a magnified view of a distal tip of the delivery tool to highlight delivery tool features.
Figure 3:
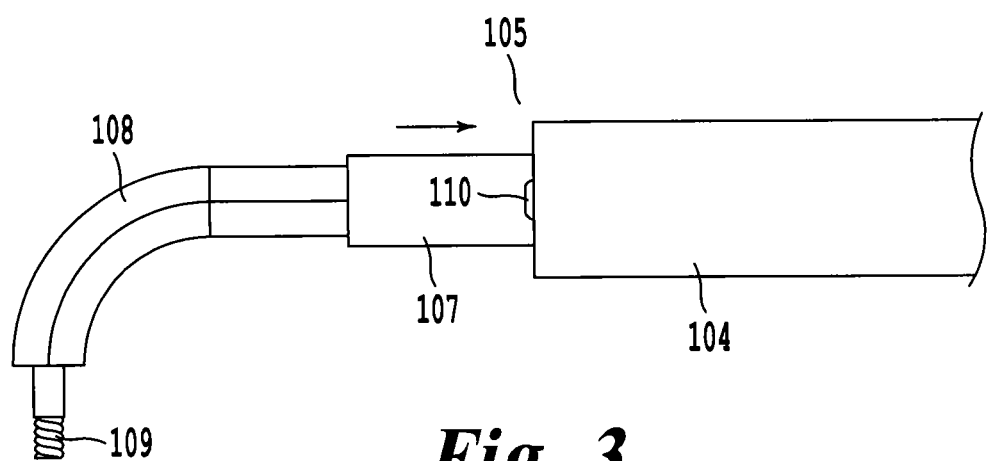
FIG. 3 illustrates a top down view of the distal tip illustrating articulation of a pre-shaped catheter.

It is intended that access of the pericardial space and implantation of a medical device be performed through the working channel 103 of the delivery tool. FIG. 2 illustrates a magnified view of the distal tip 105 to highlight a guide sheath 107 and a pre-shaped catheter 108 within the working channel 103 of the delivery tool 100. The guide sheath 107 can extend beyond the distal tip 105 and can slide proximal with respect to the pre-shaped catheter 108 to provide an additional two degrees of freedom (DOF), rotating a cardiac pacing lead 109 up to 90° with respect to the camera channel 104 as illustrated in FIG. 3.

In another embodiment of the device, the pre-shaped catheter 108 is composed of a memory shaped alloy. The catheter may be one solid piece, or a combination of smaller coaxial segments that are selectively coupled. The memory shaped alloy can be pre shaped to any configuration, and may be shaped based on patient anatomy observed with a preoperative scan. When located within the device, the memory alloy catheter forms to the working channel 103 of the delivery tool 100. When extended beyond the working channel 103 of the core 102, the catheter 108 returns to its pre-bent state.

Figure 4:
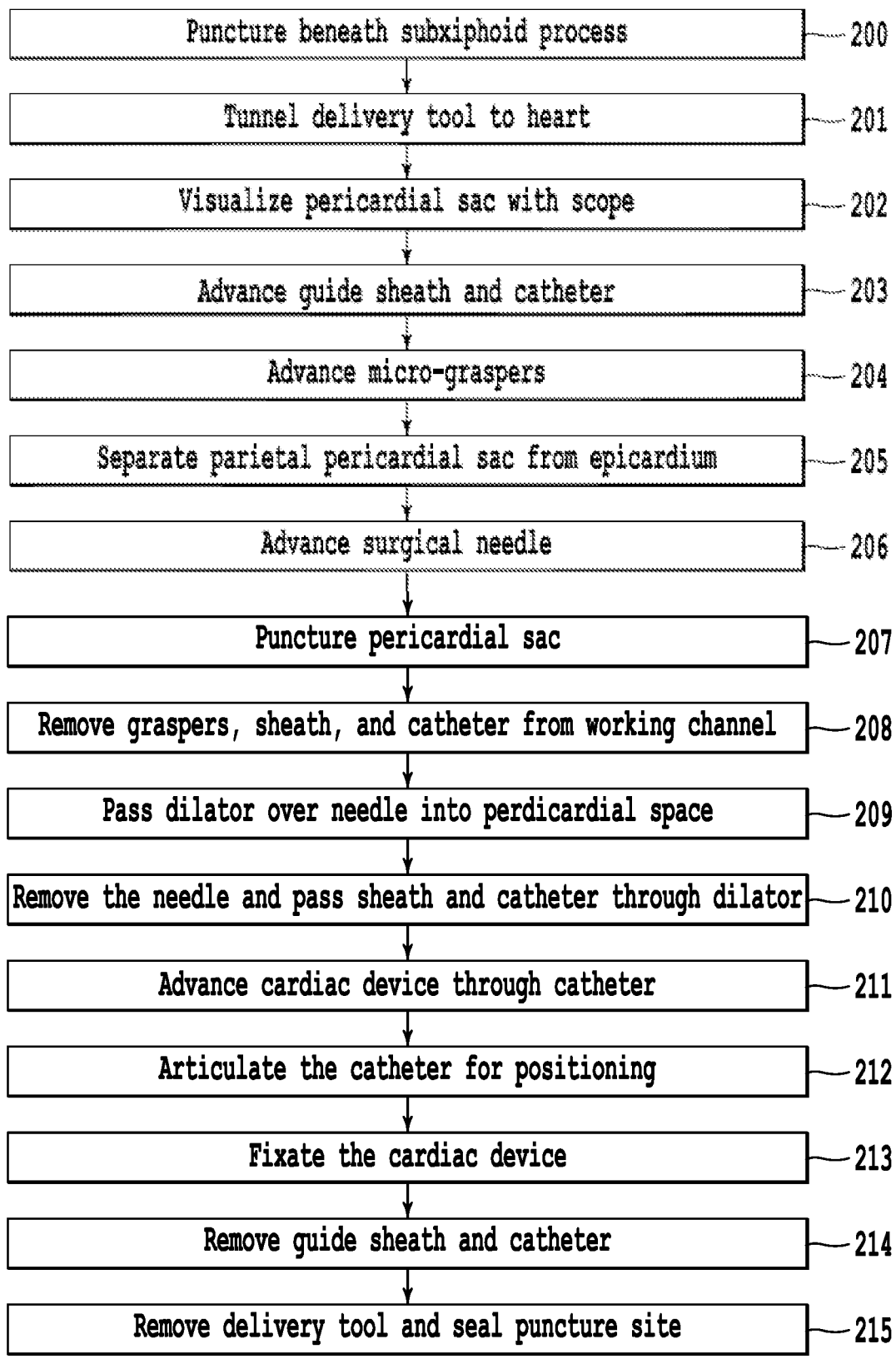
FIG. 4 illustrates a clinical workflow for using the delivery tool to place a cardiac device.

FIG. 4 illustrates a workflow for the method of implanting a medical device using the epicardial delivery tool 100 under percutaneous technique. The procedure begins by identifying and making an incision beneath the subxiphoid process (200). Tissue is dissected from the subxiphoid incision to the apex of the heart. The delivery tool is passed through a trocar spanning from the subxiphoid incision into the left hemithorax, where the apex of the heart and pericardial sac (201) can be observed under direct visualization (202) from a camera 110. The guide sheath 107 and pre-shaped catheter 108 are advanced through the working channel 103 of the delivery tool until observed by the camera 110 at the distal tip 105 of the delivery tool (203). Micro-graspers 301 are advanced (204) through the pre-shaped catheter 108 until they extend beyond the distal tip 105 of the delivery tool 100. The micro-graspers 301 are used to separate (205) the pericardial sac 304 from the epicardial surface 305. A surgical needle 302 is advanced (206) through the working channel 103 of the delivery tool 100 until it is observed at the distal tip 105. While still grasping the pericardial sac, the surgeon injects saline through the surgical needle 302 while simultaneously puncturing (207) the pericardial sac 304.

Once the pericardial sac 304 is punctured, the micro-graspers 301, the pre-shaped catheter 108 and guide sheath 107 are removed (208) from the working channel 103 of the delivery tool 100. A dilator is passed (209) over the surgical needle 302, enlarging the puncture in the pericardial sac 304. The guide sheath 107 and pre-shaped catheter 108 are passed though the lumen of the dilator (210) into the pericardial space 307. The dilator is removed from the working channel 103 of the delivery tool 100. A cardiac pacing lead 109 is advanced through (211) the pre-shaped catheter 108 and into the pericardial space 307. The guide sheath 107 slides proximally with respect to the pre-shaped catheter 108, articulating (212) the cardiac lead 109 up to 90°. The pacing lead 109 is advanced through the pre-shaped catheter 108 and anchored (213) to the epicardial surface 305 through manual rotation of the cardiac lead 109. The pre-shaped catheter 108 and guide sheath 107 are removed (214) from the working channel 103 of the delivery tool 100. The epicardial delivery tool 100 is removed from the subxiphoid incision (215). The pacing lead 109 is connected to an implanted pacemaker. The subxiphoid incision is closed.

Figure 5:
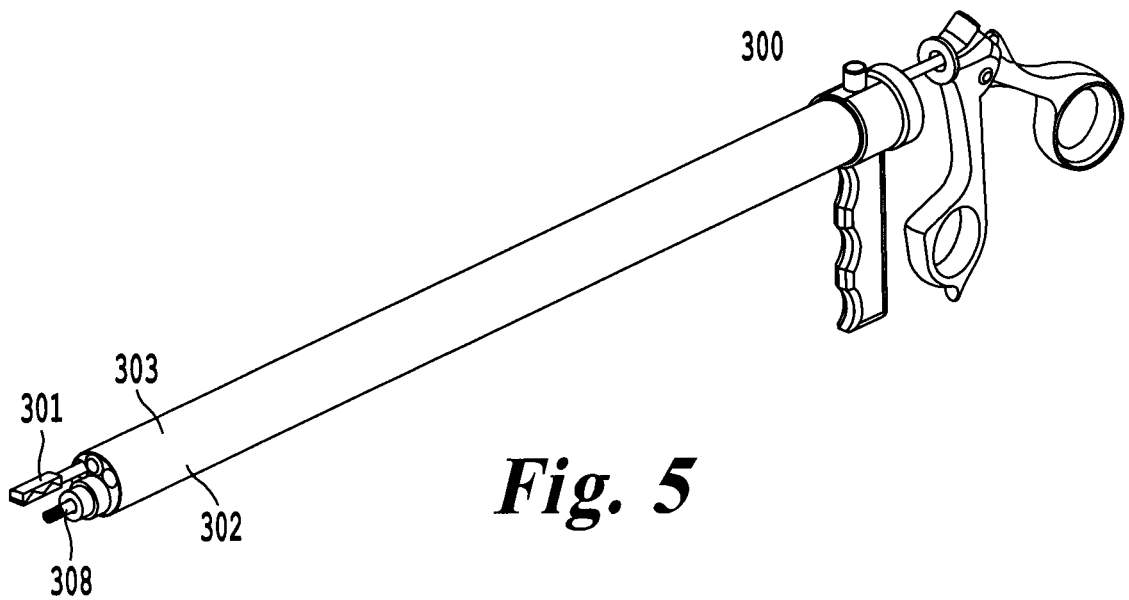
FIG. 5 illustrates an exemplary embodiment of the delivery tool including multiple working channels for surgical tools.
Figure 6:
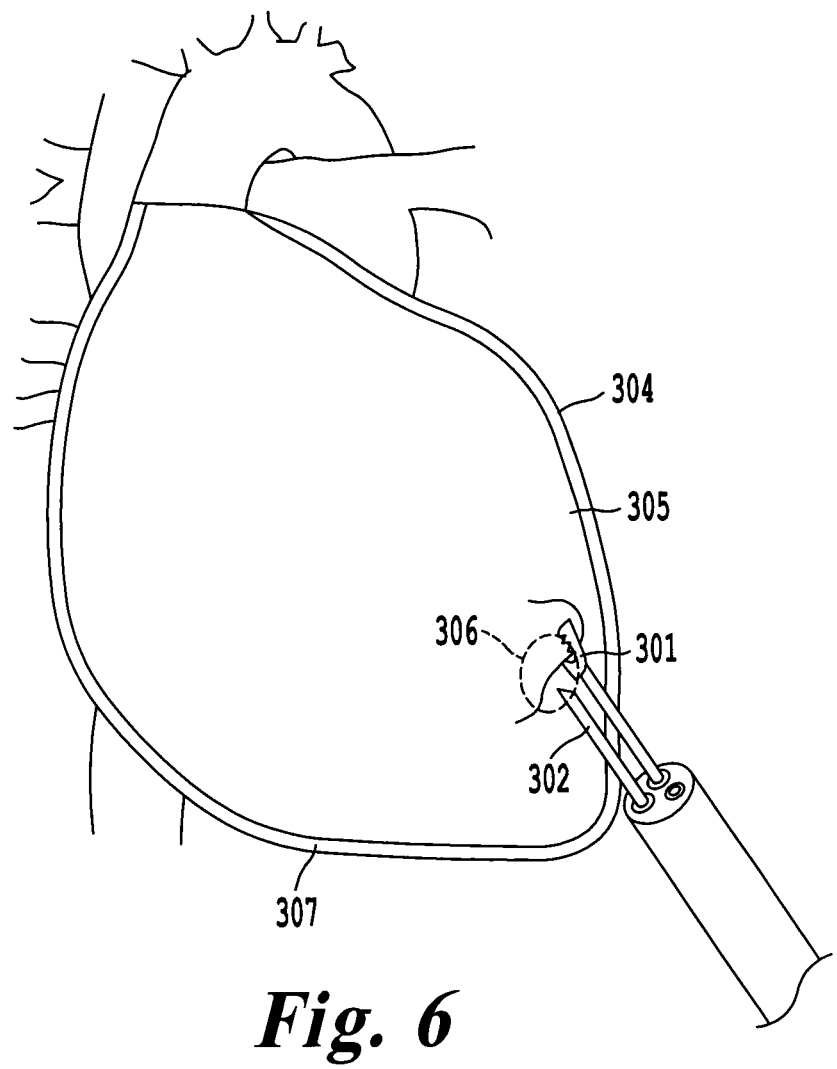
FIG. 6 illustrates grasping pericardium with micrograspers for safe needle puncture of the pericardial sac.

In another exemplary embodiment of the delivery tool 300 illustrated in FIG. 5, there is described multiple working channels which may be used interchangeably to deliver cardiac devices to the epicardial space with a subxiphoid approach. This configuration can provide better control over access to the pericardial space. A first working channel 302 facilitates the delivery of the cardiac device 308, while the second working channel 303 is dedicated to guide surgical tools such as micro-graspers 301 to the surgical site. These surgical tools can be used to grab and separate the pericardial sac 304 from the epicardial surface 305, providing a safe region 306 where a puncture can take place as shown in FIG. 6. Electrocautery hooks or ablation tools can also be inserted to selectively burn an opening in the pericardial space 307. After accessing the pericardial space 307, delivery of the cardiac device 308 may be completed as described in FIG. 4.

The first working channel 303 can also be used to deliver surgical tools to manage the surgical site. One such example would be providing an irrigation tube to clear the visual field with saline or suction. A second example includes the use of a biopsy punch to sample tissue during a subxiphoid approach. The second working channel 303 can also be used to simultaneously deliver a second cardiac device to the pericardial space 307. Deflectable, pre-shaped, and malleable catheters can be used in this working channel to selectively position the surgical tools or cardiac devices.

Alternatively, the additional working channels may be used to deliver imaging technology to the pericardial space for multimodal diagnostic imaging. In one embodiment, the imager could be an ultrasound transducer capable of scanning the pericardial surface of the heart. If placed in the pericardial space, the ultrasound transducer may be used to image the epicardial surface of the heart. Alternatively, a multispectral light guide or camera may be placed in the working channel to illuminate or image the pericardial sac, pericardial space, or epicardial tissue of the heart. At least one additional wavelength may be emitted from the multispectral imaging system. Different illumination wavelengths may increase the visibility of different anatomical structures. Any combination of one or more imaging technologies may be used to detect structures not readily visible under direct visualization such as the coronary artery with an obliterated pericardial space.

Figure 7:
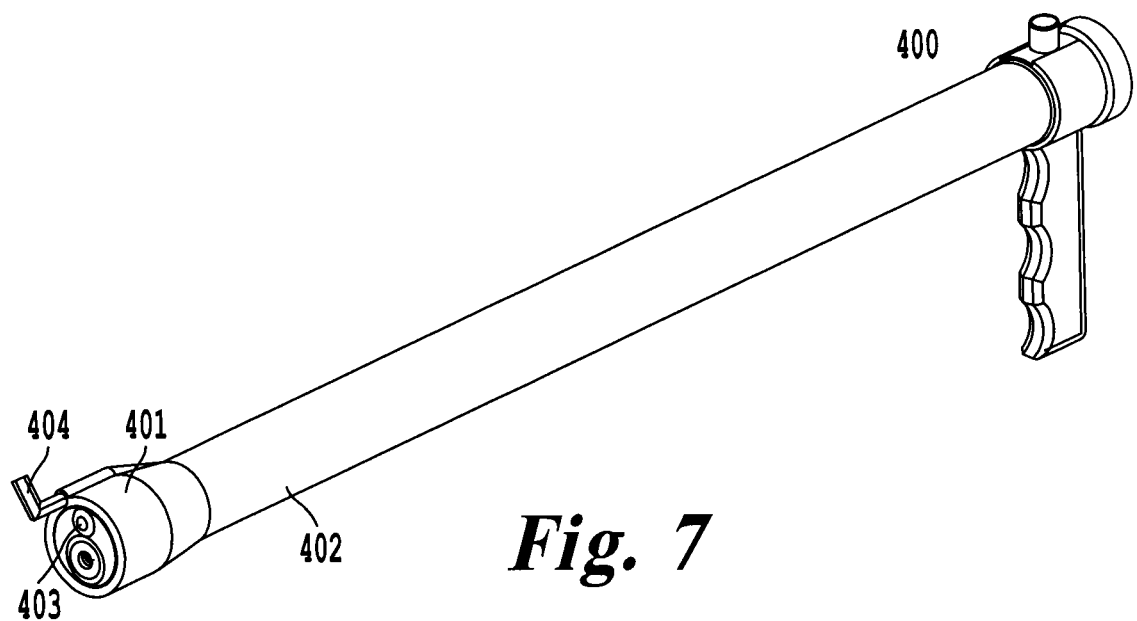
FIG. 7 illustrates an exemplary embodiment of the delivery tool shown with an electrocautery hook as a detachable surgical tool.
Figure 8:
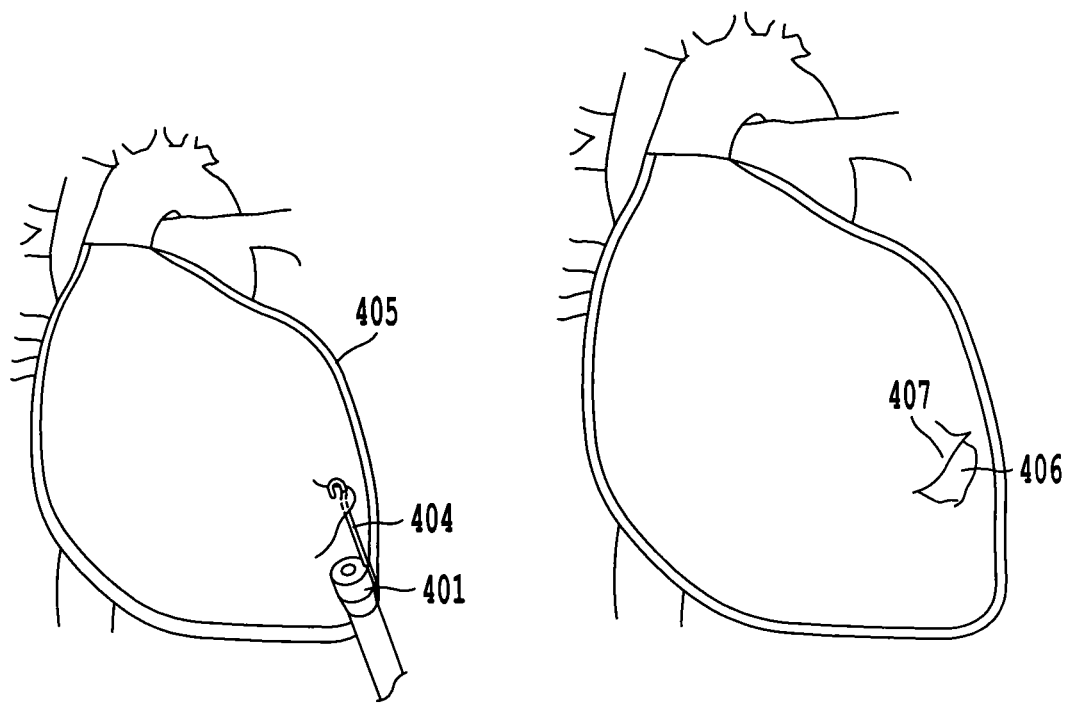
FIG. 8 illustrates cutting a hole in the pericardial sac using an electrocautery hook as a detachable surgical tool on the delivery tool.

Another exemplary embodiment of the delivery tool 400 includes detachable surgical tools 401 at the distal end of the delivery tool 400, as illustrated in FIG. 7. The surgical tools 401 can be used to selectively target and cut pericardial tissue so that delivery of a device such as the cardiac device 101 can be performed through working channel 402 under direct visualization of camera 403. An electrocautery hook 404 is shown in FIG. 8 to illustrate how the pericardial sac 405 can be cut 406 and accessed using a detachable surgical tool 401. In this embodiment, the cutting action is performed by the surgeon manipulating the delivery tool 400 so that the pericardial sac 405 is caught on the surgical hook 404. By depressing a switch, the surgeon can electrify the hook 404 and selectively cut the tissue 407. Once the pericardial space is opened, the cardiac device can be delivered to the pericardial space through the working channel 402 as described in FIG. 4.

Figure 9:
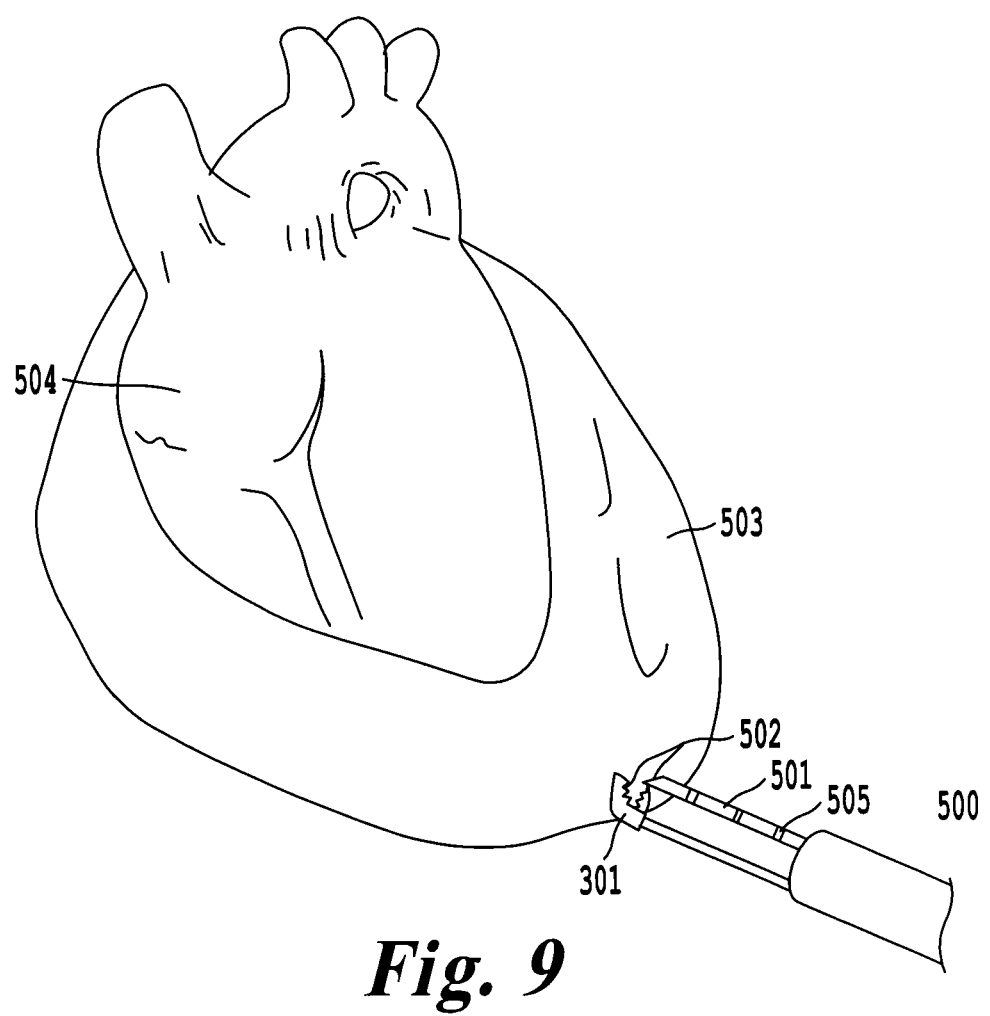
FIG. 9 illustrates an exemplary embodiment using a force sensing needle to safely puncture the pericardium.

Another exemplary embodiment of the delivery tool 500 includes a force sensing needle 501 capable of providing feedback to the surgeon, such that the pericardial space 502 can be safely accessed. FIG. 9 illustrates a surgeon using the force sensing needle 501 and micro-graspers 301 to safely puncture the pericardial sac 503. One strategy includes using force feedback to indicate a safe region of force that punctures the pericardial sac 503, but does not puncture the epicardial surface 504. Force sensing can be achieved by incorporating miniaturized sensors 505 such as a strain gauge, a pressure sensor, or an optical sensor within the needle body, or along the needle length. In this embodiment once the pericardial space 502 has been accessed, the cardiac device can be implanted using the approach described in FIG. 4.

Figure 10:
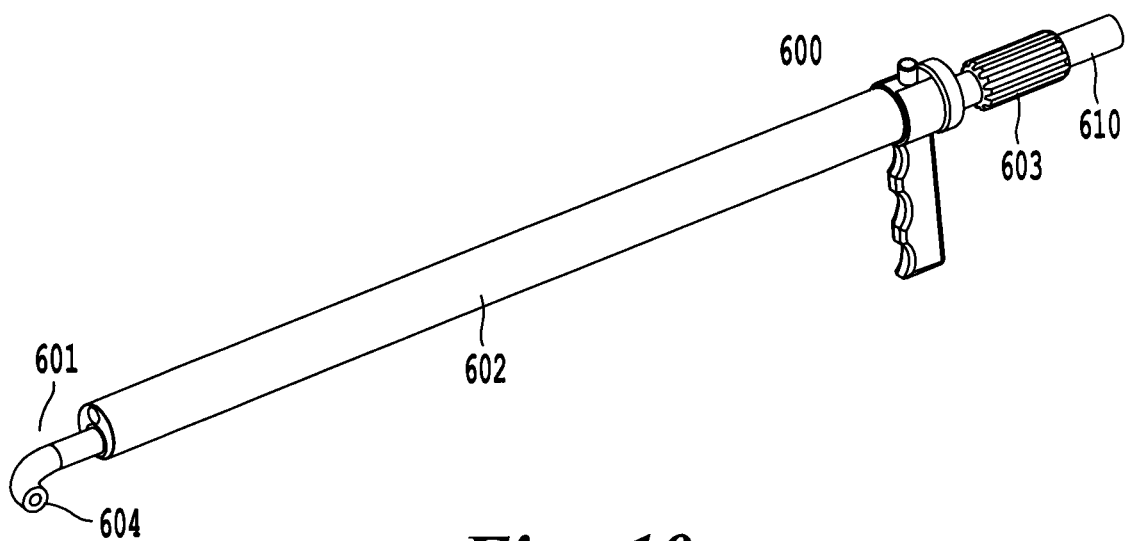
FIG. 10 illustrates an exemplary embodiment using a deflectable catheter to selectively position a medical device.
Figure 11:
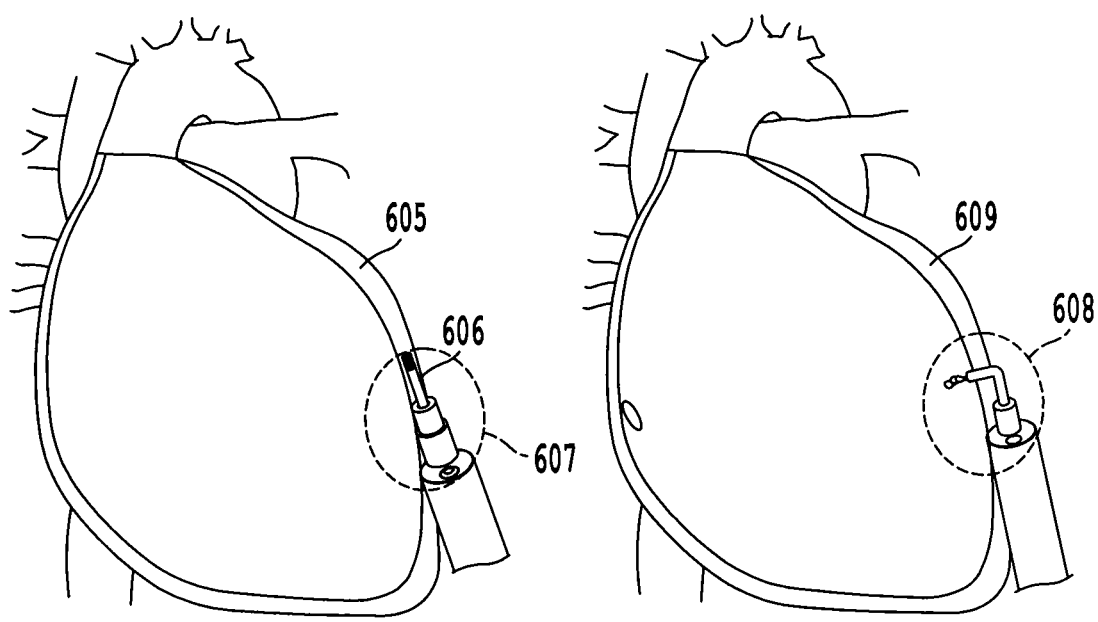
FIG. 11 illustrates articulating the deflectable catheter for selective placement of the medical device tangential or normal to the epicardial surface.

In another exemplary embodiment of a delivery tool 600, selective placement of the cardiac device in the pericardial space 307 may be accomplished with a deflectable or steerable catheter 601 in place of the guide sheath 107 and pre-shaped catheter 108. FIG. 10 illustrates a steerable catheter 601 placed in the working channel 602 of the delivery tool 600. Rotation of an articulation knob 603 provides 0-90° bending of the catheter's distal tip 604, while a second degree of freedom can be implemented by rotating the entire catheter 601. Once the pericardial space 605 has been dilated and accessed, the deflectable catheter 601 can be positioned inside the pericardial space 605, and articulated to provide selective placement of the cardiac device 606. The additional degrees of freedom allow the cardiac device 606 to be positioned both tangentially 607 and normal 608 to the epicardial surface 609 for proper fixation as shown in FIG. 11.

Additionally, the steerable catheter 601 may include a locking knob 610 capable of restricting articulation of the tool to a desired angle. In another embodiment of the device, the steerable catheter is composed of a memory shaped alloy. The catheter may be one solid piece, or a combination of smaller coaxial segments that are selectively coupled. The memory shaped alloy can be pre-shaped to any configuration, and may be shaped based on patient anatomy observed with a preoperative scan. When located within the device, the memory-alloy-catheter forms to the working channel of the delivery tool. When extended beyond the working channel of the tool, the catheter conforms to its pre-bent state.

Figure 12:
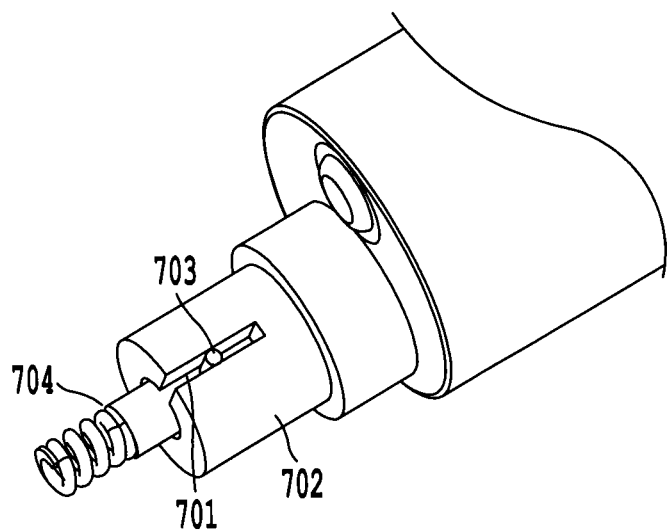
FIG. 12 illustrates an exemplary embodiment using a locking feature to engage and rotate a cardiac device for placement and fixation.
Figure 13:
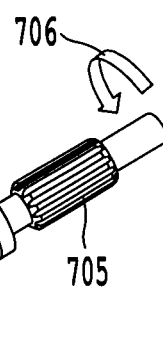
FIG. 13 illustrates rotation of a sheath that provides one to one rotation of the medical device at the tip.

Another exemplary embodiment of the delivery tool 700 utilizes a locking member 701 of the catheter 702 to detachably engage a feature 703 on the cardiac device 704. As illustrated in FIG. 12, the locking member 701 of the catheter 702 can be a cut or groove-sized to catch a raised element (feature 703) of the cardiac device such a tangential pacing barb on a cardiac pacing lead. Alternatively the locking member 701 of the catheter 702 can be a raised feature to selectively engage a groove on the cardiac device 704. Both the locking member 701 of the catheter and specialized element (feature 703) comprise a method to selectively couple the catheter 702 to the cardiac device 704. Both features may be used to couple each component at more than one location. Once the catheter 702 is selectively coupled to the cardiac device 704, rotation of a handle 705 connected to catheter 702 provides one-to-one rotation 706 of the cardiac device 704 as illustrated in FIG. 13. This rotation may be used to orient or fixate the cardiac device 704 in the pericardial space 605.

Figure 14:
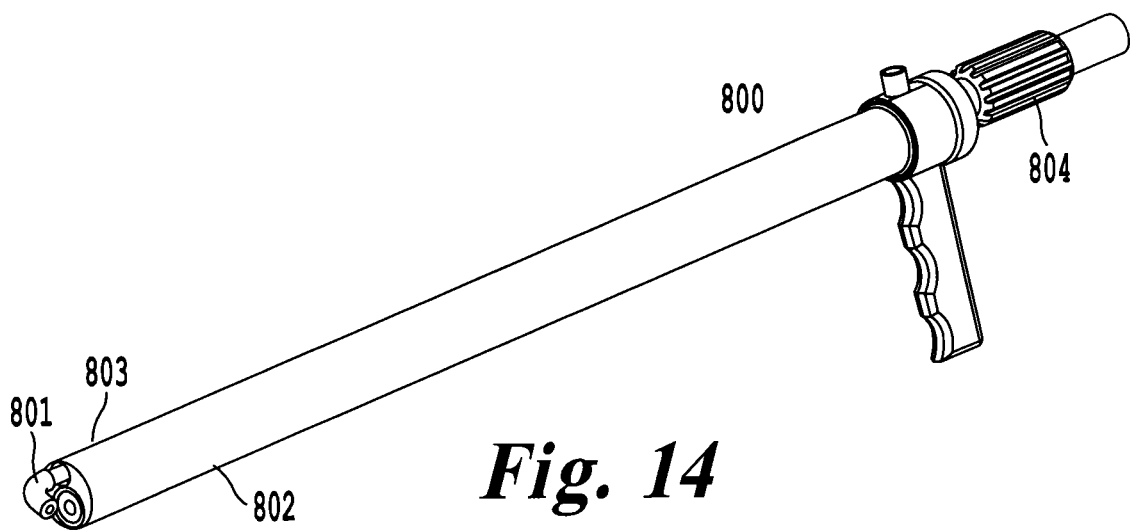
FIG. 14 illustrates an exemplary embodiment using a deflectable camera to provide additional viewing angles for the delivery tool.
Figure 15:
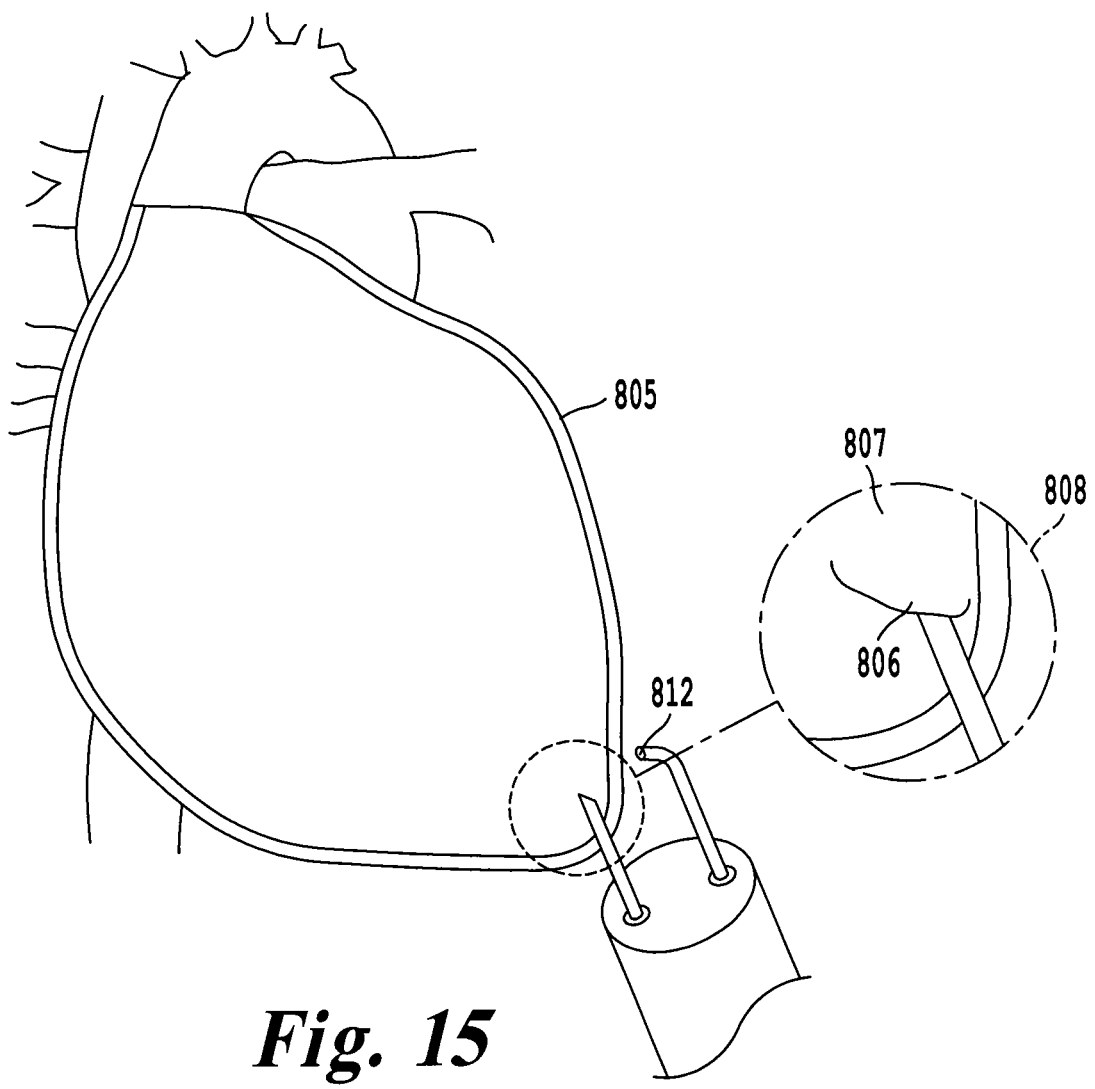
FIG. 15 illustrates an additional viewing angle provided by the deflectable camera showing the needle moving tangentially to the pericardial sac, instead of normal to the pericardial sac.

For an inline, subxiphoid approach, it is desired to have direct visualization of the surgical field including but not limited to the distal end of the delivery tool and distal tip of a device such as the cardiac device 101. FIG. 14 illustrates another exemplary embodiment of the delivery tool 800 that incorporates a deflectable camera 801 to be used with a rigid working channel 802. After the delivery tool 800 has been tunneled subxiphoid to the surgical site, the deflectable camera 801 can be advanced past the distal tip 803 of the tool 800. Rotation of an articulation knob 804 provides 0-90° bending of the distal tip 803 of the camera 801. The additional degree of freedom at the distal tip 803 provides both a tangential and normal view of the heart 804, which can be used to properly visualize the pericardial sac 805 for a safe puncture 806. Additionally, the articulation can be used to visualize anatomy not readily visible behind the heart with the subxiphoid approach such as the great cardiac vein 807. The deflectable camera may also contain one or more working channels 812 through which surgical tools can be placed to assist with the procedure. FIG. 15 illustrates the additional view 808 in which the deflectable camera 801 can provide to selectively fixate the cardiac device under direct visualization. In another embodiment, the deflectable camera 801 can be extended into the pericardial sac 805 to provide direct visualization of the pericardial space. Visualization of the pericardial space allows the surgeon to identify elements not readily visible with a direct line of sight. Visualization of the pericardial space allows the surgeon to observe fixation of the cardiac device.

Figure 16:
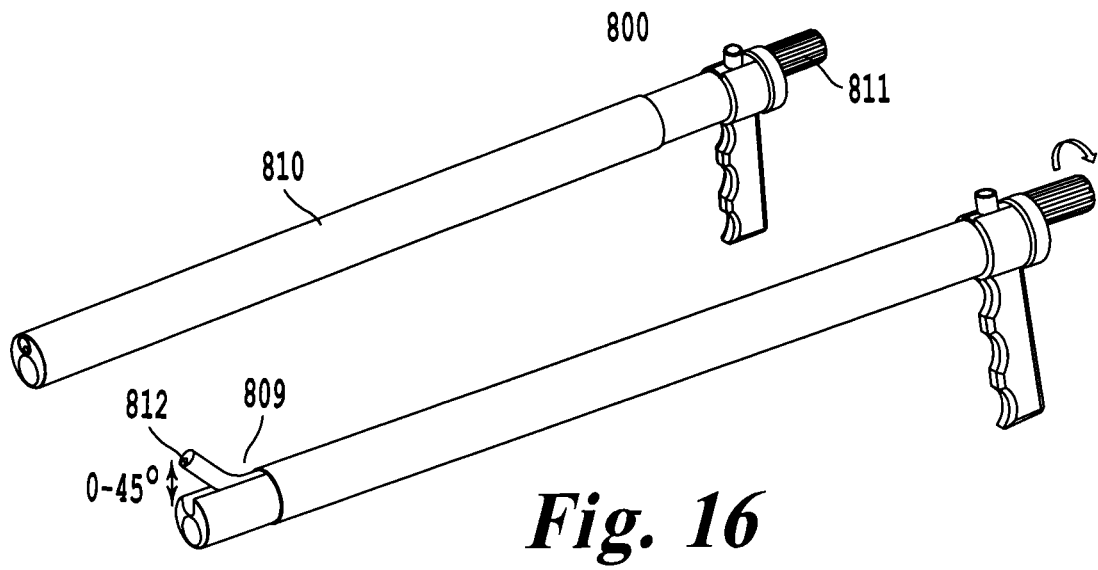
FIG. 16 illustrates an exemplary embodiment incorporating a deflectable working channel for the deflectable scope so that a larger surgical field of view can be obtained.

In another exemplary embodiment, the deflectable camera 801 is passed through a deflectable working channel 809 and exits the side wall of the delivery tool 800 as illustrated in FIG. 16. The deflectable camera 801 is housed in a working channel that is formed in the outer surface of the core toward the center of the core. The deflectable working channel 809 can be made from a super elastic material such as nitinol, pre-shaped tube, or deflectable catheter. The deflectable working channel 809 allows the deflectable camera 801 to be positioned further from the surgical site to provide a wider field of view. The deflectable working channel 809 can be selectively bent such that the exit angle of the deflectable camera 801 is between 0-45°. Selective flexion of the deflectable working channel 809 is achieved by sliding an outer sheath 810 along the body of the delivery tool 800. When the outer sheath 810 has been fully extended, the outer sheath restrains the deflectable working channel 809 to a view in line with the tool 800. As the outer sheath 810 is retracted, the deflectable working channel 809 is allowed to return to its pre-bent shape as illustrated in FIG. 16. The outer sheath 810 can be slid along the delivery tool 800 manually, or may be connected to a linear screw mechanism 811. Rotation of a handle connected to the linear screw 811 engages the outer sheath 810 sliding the outer sheath over the delivery tool 800.

Figure 17:
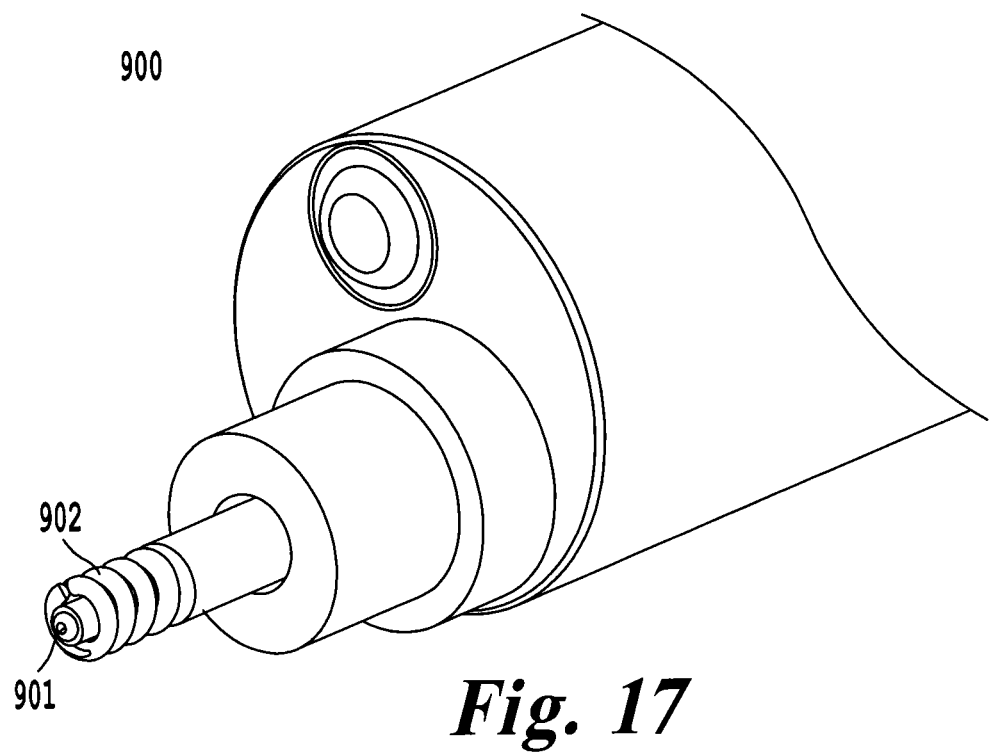
FIG. 17 illustrates an exemplary embodiment incorporating a micro camera within the medical device.
Figure 18:
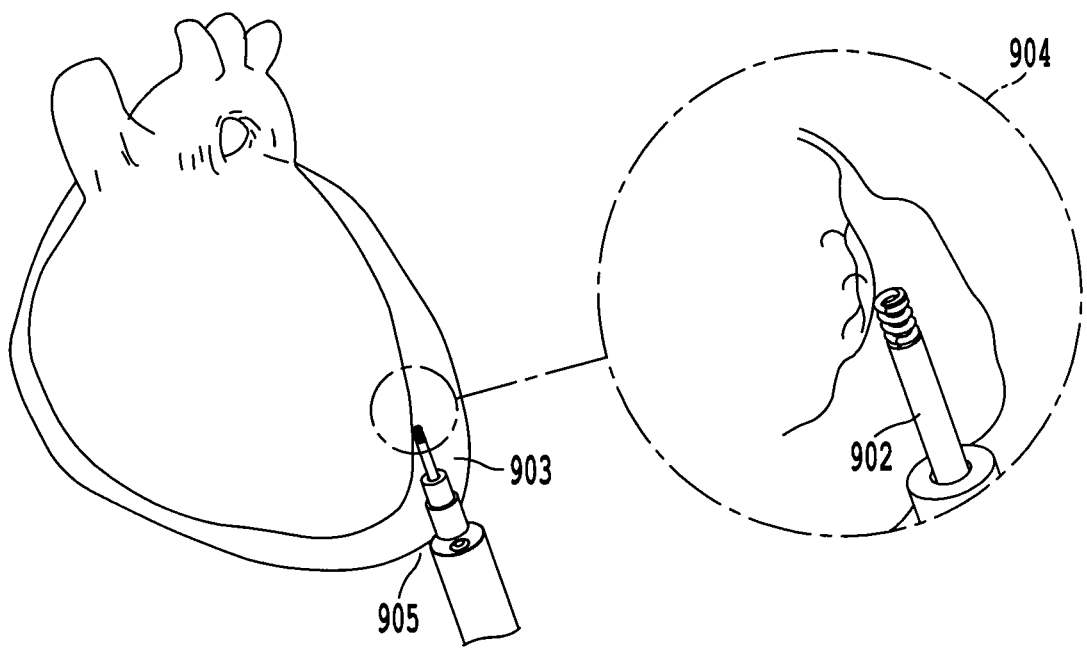
FIG. 18 illustrates two views that can be seen with the delivery tool camera, and the micro camera attached to the cardiac device.

In another exemplary embodiment of a delivery tool 900, a micro camera 901 may be attached or detachably attached to the cardiac medical device 902 to be implanted. FIG. 17 illustrates positioning of the micro camera 901 down the lumen of a cardiac pacing lead 902 to provide a coaxial view of the surgical field. After gaining access to the pericardial space 903, the cardiac device 902 can be selectively positioned in the pericardial space 903 using either a steerable catheter, or pre-shaped catheter and guide sheath. Direct visualization of the distal tip 904 of the cardiac device 902 is maintained throughout the surgical procedure to ensure the device 902 is secured in the correct anatomy. After the cardiac device 902 is fixated in the pericardial space 903, the micro camera 901 can be detachably released and removed. FIG. 18 illustrates the two views available to a surgeon when using the camera of the delivery tool 900, as well as the micro camera 901 detachably attached to the cardiac device 902. The two views allow the surgeon to maintain visualization of both the entry of the cardiac device into the pericardial space 905, as well as the distal tip 904 of the cardiac device 902.

Figure 19:
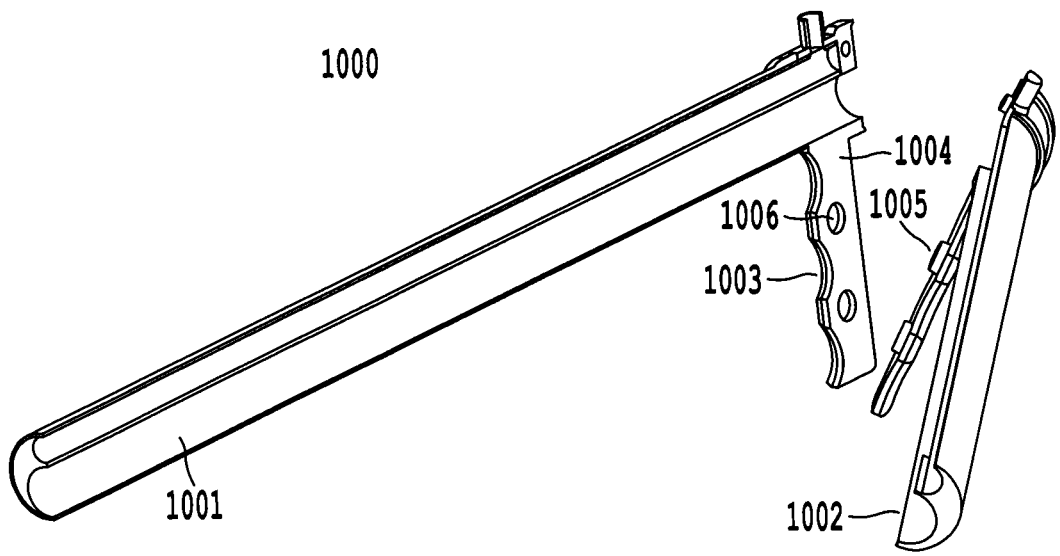
FIG. 19 illustrates an exemplary embodiment of a breakable delivery tool featuring locking keys and grooves.

In another exemplary embodiment, a selectively breakable delivery tool 1000 is presented for the subxiphoid approach. The ability to break the delivery tool 1000 in two parts allows the delivery tool 1000 to be miniaturized such that the limiting factor is a feature of the cardiac device to be implanted. In an exemplary embodiment, the delivery tool 1000 breaks into two equal halves. In this instance, the working channel 1001 of the delivery tool 1000 can be minimized to accommodate just the body of the pacing lead. After the lead has been positioned with the aid of a pre-shaped or deflectable catheter, the delivery tool 1000 can be separated along part line 1002 by applying a force normal to separation groves 1003 on tool body 1004. Once separated, the delivery tool 1000 can be separated from the cardiac device. FIG. 19 illustrates the delivery tool 1000 after the delivery tool has been split in half. Locking keys 1005 and holes 1006 are used to selectively couple the halves of the tool 1000 together. Proper alignment of the halves may be guaranteed by unique key shape, placement, or any combination thereof. In once embodiment, there may exist three cylindrical pins embedded in one half of the body of the delivery tool. In the mirrored half of the delivery tool, there may exist three holes that accept the cylindrical pins. When brought together, the pins align with the holes, and the two halves of the tool body interlock.

Figure 20:
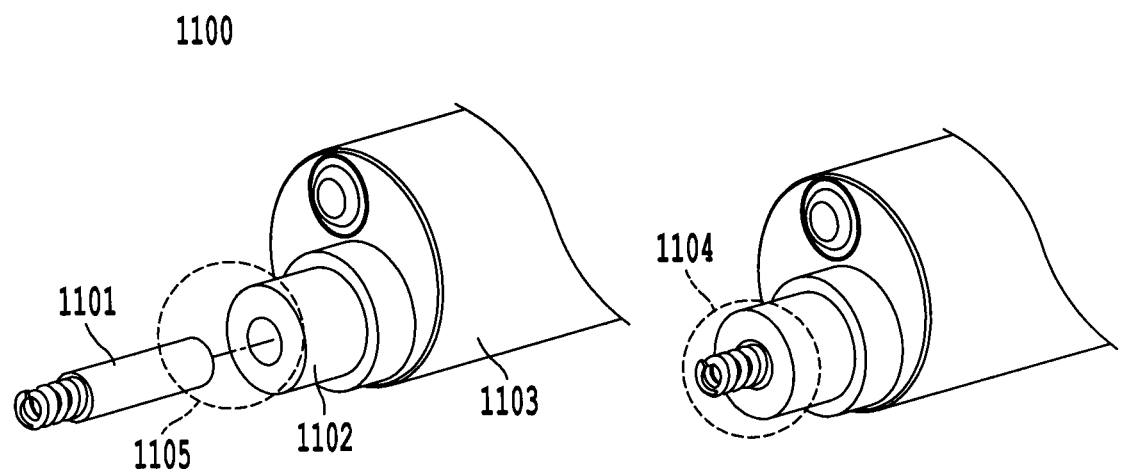
FIG. 20 illustrates an exemplary embodiment where the cardiac device is a leadless pacemaker that can be selectively coupled and decoupled from the catheter using a press fit.

In another exemplary embodiment, the epicardial delivery tool 1100 is designed to accommodate a leadless pacemaker 1101 for fixation in the pericardial space. The leadless pacemaker 1101 may be selectively coupled and decoupled from either an unshaped, pre-shaped, or deflectable catheter 1102 that is passed through the working channel 1103 of the delivery tool 1100. Visualization of the surgical field is provided by camera 1104 of the delivery tool 1100. The leadless pacemaker 1101 may be press fit into the catheter 1102, and maintain orientation within the tool 1100 via friction between the pacemaker 1101 and the catheter 1102. After gaining access to the pericardial space, the catheter may be manipulated within the working channel 1103 of the delivery tool 1100 to properly position the leadless pacemaker 1101 against the epicardial surface. Rotation of the catheter 1102 provides direct torque to the leadless pacemaker 1101, facilitating fixation to the epicardial surface. When the catheter 1102 is removed from the delivery tool 1100, the leadless pacemaker 1101 disengages from the delivery tool 1100. The force required to press fit the leadless pacemaker 1101 inside the catheter 1102 is large enough to allow rotation of the catheter 1102 to fixate the device 1101, but small enough to allow the leadless pacemaker 1101 to separate from the catheter 1102 when the catheter is removed from the working channel 1103. FIG. 20 illustrates a leadless pacemaker 1101 coupled 1104 and selectively decoupled 1105 from the catheter 1102 within working channel 1103 of the delivery tool 1100.

Figure 21:
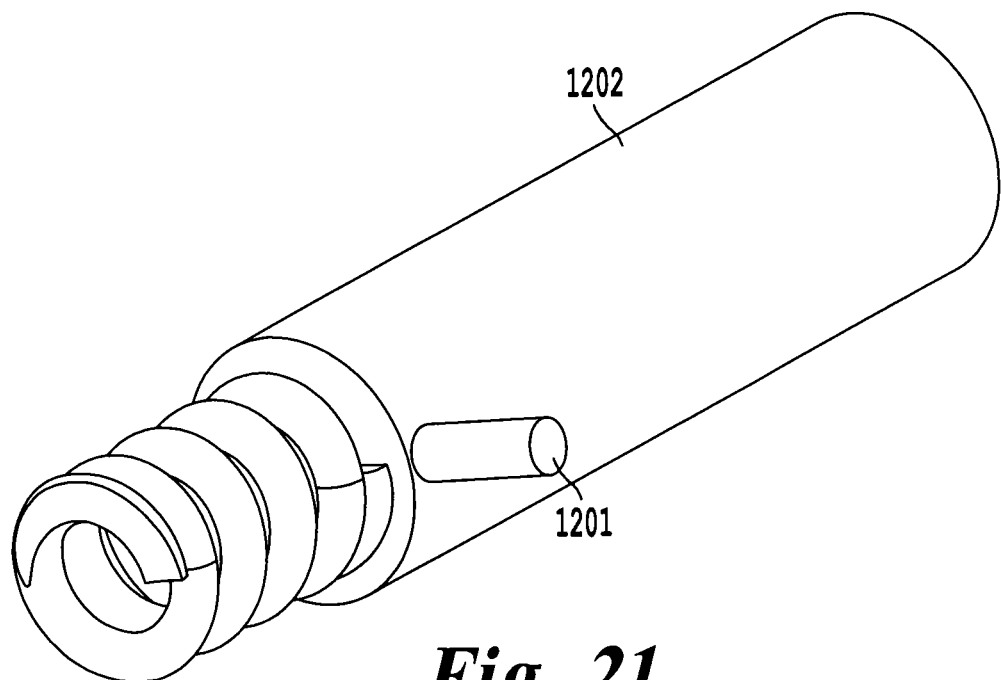
FIG. 21 illustrates an exemplary embodiment of a leadless pacemaker that includes a raised feature for selective coupling with the delivery tool.

In another exemplary embodiment of a delivery tool 700, a locking member 701 of the guide sheath or catheter 702 may detachably engage a feature 1201 on the leadless pacemaker 1202. As illustrated in FIG. 12, the locking member 701 of the guide sheath 702 can be a cut or groove-sized to catch a raised element (feature 1201) of the leadless pacemaker 1202 such as a tangential pacing barb or fixation hook 1201 as shown in FIG. 21. Alternatively the locking member of the sheath can be a raised feature to selectively engage a groove on the leadless pacemaker 1202. Both the locking member 701 and specialized element (feature 1201) comprise a method to selectively couple and decouple the delivery tool 700 to the leadless pacemaker 1202. Both features may be used to couple each component at more than one location. Once the catheter 702 is selectively coupled to the leadless pacemaker 1202, rotation of the guide sheath handle 705 provides one-to-one rotation 706 of the leadless pacemaker 1202. This rotation may be used to orient or fixate the leadless pacemaker 1202 in the pericardial space. The guide sheath may have a secondary feature to ensure that back rotation of the guide sheath 702 does not decouple the leadless pacemaker 1202 from the guide sheath 702. After the leadless pacemaker 1202 has been fixated to the epicardial surface, the guide sheath 702 may be rotated and orientated in a way as to selectively decouple the locking groove 701 from the raised feature 1201.

Figure 22:
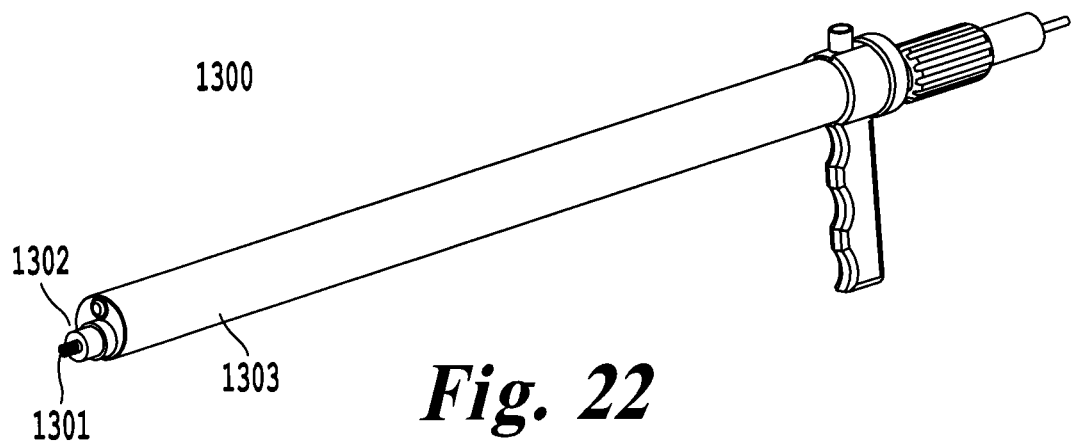
FIG. 22 illustrates an exemplary embodiment of the tool where the leadless pacemaker is free to move within the tool and catheter.
Figure 23:
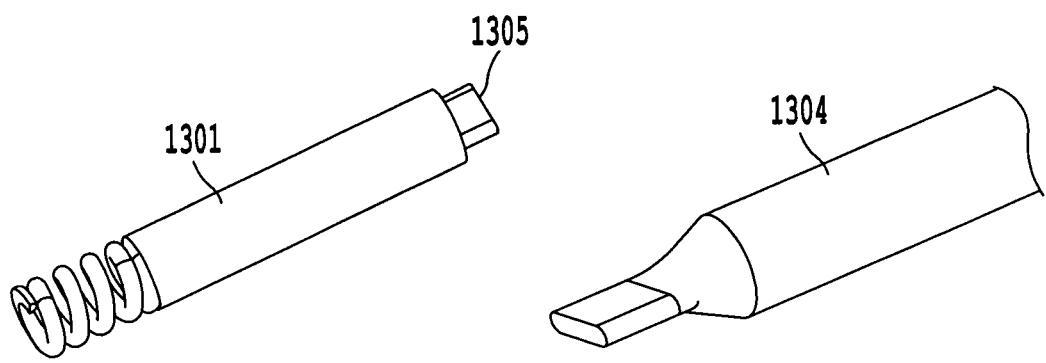
FIG. 23 illustrates a leadless pacemaker and torque tool highlighting the interlocking interface to control positioning and fixation of the pacemaker.

In another exemplary embodiment of a delivery tool 1300, the leadless pacemaker 1301 is free to slide within an unshaped, pre-shaped, or deflectable catheter 1302. Manipulation of the catheter 1302 in the working channel 1303 of the delivery tool 1300 allows the leadless pacemaker 1301 to be selectively positioned against the epicardial surface in the pericardial space. FIG. 22 illustrates the delivery tool 1300 of this design, with accompanying leadless pacemaker 1301 and torque tool 1304 shown in FIG. 23. The leadless pacemaker 1301 has pocket 1305 capable selectively engaging or disengaging torque tool 1304. Selective engagement may be provided by magnetism or another force of the like. The torque tool 1304 is inserted into pocket 1305 and used to stabilize the leadless pacemaker 1301 within the catheter 1302. Once the catheter 1302 has selectively positioned within the epicardial space, the leadless pacemaker 1301 may be advanced through the catheter 1302 by manipulation of the torque tool 1304. Rotation of the torque tool 1304 transmits one-to-one force directly to the lead less pacemaker 1301, allowing the surgeon to fixate the pacemaker in the pericardial space. Once the leadless pacemaker 1301 has been fixated, the torque tool 1304 is disengaged from the leadless pacemaker 1301 by removing it from the catheter 1302. The force required to couple the leadless pacemaker 1301 to the torque tool 1304 is large enough to allow rotation of the catheter 1302 to fixate the device 1301, but small enough to allow the leadless pacemaker 1301 to separate from the torque tool 1304 when an axial force is applied.

Figure 24:
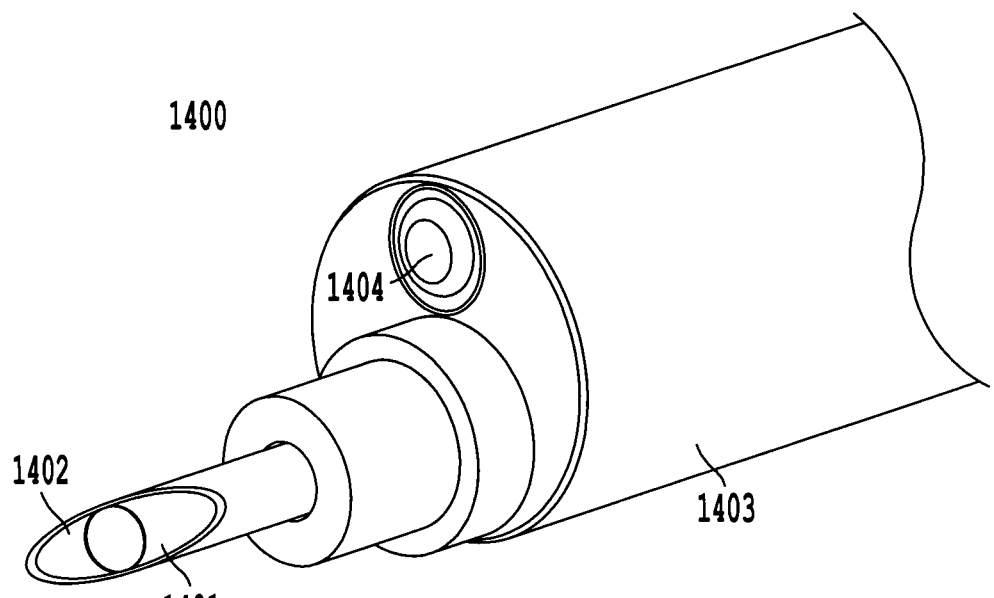
FIG. 24 illustrates an exemplary embodiment where the delivery tool is used to deliver a micro pacemaker for fetal pacing.

In another exemplary embodiment, a delivery tool 1400 is used to deliver a micro pacemaker 1401 within the epicardial tissue as shown in FIG. 24. For this application, a needle 1402 is positioned within the working channel 1403 of the delivery tool 1400. The needle 1402 has a micro pacemaker 1401 press fit within the lumen. Applications for a micro pacemaker may include fetal pacing. When the pericardial sac has been isolated under visualization of the camera 1404 in the delivery tool 1400, the needle 1402 is advanced into the pericardial sac. Intraluminal pressure may release the micro pacemaker from the needle 1402, injecting the micropacemaker 1401 into the pericardial space. Fixation of the micro pacemaker 1401 is accomplished by friction between the pericardial sac and the epicardial surface. The needle 1402 can be removed from the pericardial space, and withdrawn from working channel 1403. In another embodiment of the device, the delivery tool 1400 may be used to deliver therapeutic agents to the epicardium, pericardium, or pericardial space under direct visualization. The therapeutic agents may be stem cells for regenerative therapy. The therapeutic agents may be pharmaceuticals for drug induced therapy. The therapeutics may be delivered with the use of a needle 1402 that has been passed through the working channel of the delivery tool 1400.

Figure 25:
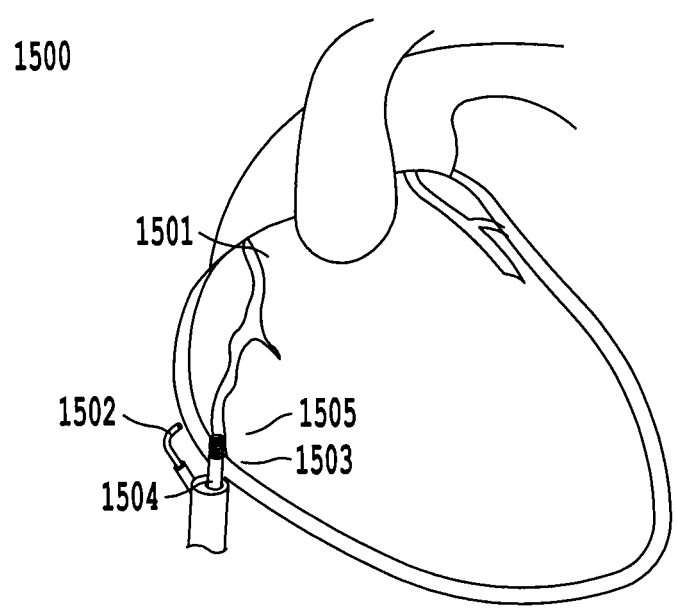
FIG. 25 illustrates an exemplary embodiment where the delivery tool is used to deliver therapy devices such as stents to the coronary arteries under direct visualization of the deflectable camera.

In another exemplary embodiment, a delivery tool 1500 can be used to delivery therapy devices to the coronary arteries 1501. Using the same approach outlined in FIG. 4, the coronary arteries 1501 can be accessed and visualized under direct visualization of the deflectable camera 1502 as shown in FIG. 25. Once the coronary arteries 1501 are visualized, a sheath 1503 may be passed through the working channel 1504 of the delivery tool 1500 to the coronary artery 1501. A stent 1505 can be placed on a balloon catheter and advanced to the obstruction in the coronary artery 1501. The balloon can be inflated, relieving the obstruction in the coronary artery 1501 and a closure device is deployed. After the procedure, the coronary artery 1501 can be observed under direct visualization of the camera for any bleeding.

The specific embodiments described above have been shown by way of example in a surgical case and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

As used herein, the terms "comprises," "comprising," "including," and "includes" are to be construed as being inclusive and open-ended. Specifically, when used in this document, the terms "comprises," "comprising," "including," "includes," and variations thereof, mean the specified features, steps or components included in the described features of the present disclosure. These terms are not to be interpreted to exclude the presence of other features, steps or components.

What is claimed is:

1. A device configured to deliver at least one of a therapeutic device or a surgical tool into a pericardial space using a subxiphoid approach, the device comprising:
    a core body having, at a distal end, a distal surface perpendicular to a longitudinal axis of the core body, the distal surface defining a distal plane;

one or more camera channels at least partially housed within the core body and extending along the longitudinal axis of the core body, the one or more camera channels being configured to house respective one or more devices, including cameras, each configured to provide direct visualization of a surgical site;

one or more working channels extending along the longitudinal axis of the core body, the one or more working channels being configured to deliver the at least one of the therapeutic device or the surgical tool; and an outer sheath surrounding the core body and configured to move, responsive to user input, such that at least one of the one or more devices moves between a non-deflected position and a maximum deflected position without deflection of the at least one of the therapeutic device or the surgical tool, the outer sheath being slidably adjustable along the longitudinal axis of the core body such that the one or more devices move from a side of the core body between the non-deflected position and the maximum deflected position responsive to the movement of the outer sheath, wherein when the at least one of the one or more devices moves between the non-deflected position and the maximum deflected position, a distal end of the at least one of the one or more devices does not transcend the distal plane of the core body, the one or more devices at least partially contact the outer sheath, the one or more devices is deflectable from the non-deflected position toward the maximum deflected position according to a position of the outer sheath, the one or more devices is movable from the maximum deflected position to the non-deflected position according to the position of the outer sheath, and as the outer sheath slides away from a distal end of the core body, the one or more devices deflect away from the core body toward the maximum deflected position to provide a wider field of view as compared to a field of view when the one or more devices is in the non-deflected position.

2. The device of claim 1, wherein the one or more camera channels are selectively coupled to the one or more working channels.

3. The device of claim 1, wherein the one or more devices deflect between 0 and 45 degrees, with 0 degrees corresponding to the non-deflected position and 45 degrees corresponding to the maximum deflected position.

4. The device of claim 1, wherein at least one of the one or more working channels is an imaging channel extending along the longitudinal axis of the core body and configured to house a diagnostic imaging device having an imaging modality different from an imaging modality of the one or more devices of the respective one or more camera channels.

5. The device of claim 1, wherein the one or more working channels is configured to accommodate a plurality of surgical tools simultaneously at the surgical site.

6. The device of claim 1, wherein the core body is sized and shaped to be subcutaneously tunneled from an incision beneath the subxiphoid process to a heart of a patient.

7. The device of claim 1, further comprising the therapeutic device, wherein the therapeutic device is configured to be placed through a subxiphoid positioned trochar to a thoracic cavity using the one or more working channels.

8. The device of claim 1, further comprising a guide sheath and a catheter housed in the one or more working channels and extendable beyond a distal end of the core body, the guide sheath being axially extendable along the catheter.

9. The device of claim 8, wherein the catheter is pre-shaped, and when the guide sheath is axially retracted along the catheter, the catheter articulates up to 90 degrees.

10. The device of claim 9, wherein a shape of the catheter is based on anatomy of a patient observed from a preoperative scan.

11. The device of claim 8, wherein the at least one of the therapeutic device or the surgical tool is selectively engaged and disengaged from the catheter.

12. The device of claim 11, wherein a lock projects from the at least one of the therapeutic device or the surgical tool and engages with a groove in the catheter, enabling the therapeutic device or the surgical tool to selectively engage and disengage from the catheter.

13. The device of claim 1, further comprising the therapeutic device, wherein the therapeutic device is configured to be implanted and is at least one of a pacemaker lead, an implantable cardioverter-defibrillator lead, a pacemaker, a leadless pacemaker, stem cells, a needle, an ablation catheter, or a biopsy punch.

14. The device of claim 1, wherein the core body is configured to separate into two parts along an axial part line by applying a force normal to separation grooves located on the device.

15. The device of claim 1, further comprising the at least one of the therapeutic device or the surgical tool.

16. The device of claim 1, wherein an arc of a cross-section of at least one of the one or more devices is concentric with an arc of a cross-section of the core body, a circumference of at least one respective camera channels of the one or more camera channels being discontinuous, the at least one of the one or more devices being proximate to the outer sheath of the core body.

17. The device of claim 1, wherein the outer sheath is slidably adjustable along the longitudinal axis of the core body such that the outer sheath slides over the core body.

18. A device configured to deliver a surgical tool into a pericardial space using a subxiphoid approach, the device comprising:

a core body having a first end and a second end opposite the first end, the second end having a distal surface perpendicular to a longitudinal axis of the core body, the distal surface defining a distal plane;

a camera channel extending along the longitudinal axis of the core body, the camera channel being configured to house a device configured to provide direct visualization of a surgical site;

a working channel extending along the longitudinal axis of the core body, the working channel being configured to deliver the surgical tool; and an outer sheath configured to move, responsive to user input, such that the device moves between a non-extended position and a maximum extended position, without deflection of the surgical tool, to form a predetermined non-zero angle, the device being extendable from a side of the core body, wherein a distal end of the outer sheath does not transcend the distal plane of the core body, when the device moves between the non-extended position and the maximum extended position, a distal end of the device does not transcend the distal plane of the core body, the camera channel and the working channel extend along the longitudinal axis of the core body and have respective openings at the second end of the core body, and the surgical tool is extendable and retractable at the second end of the core body, the device being extendable and retractable from a side of the core body adjacent to the second end of the core body.

\* \* \* \* \*